United States Patent
Cromartie

Patent Number: 5,464,384
Date of Patent: Nov. 7, 1995

[54] ACHILLES TENDON SUPPORT BRACE

[75] Inventor: Leonardo W. Cromartie, Rembrandt Str 2A Apt 7, Wurezburg/Lengfeld, Germany, 97076

[73] Assignee: Leonardo W. Cromartie, Wuerzburg, Germany

[21] Appl. No.: 156,628

[22] Filed: Nov. 24, 1993

[51] Int. Cl.⁶ .................................................. A61F 5/00
[52] U.S. Cl. ............................... 602/27; 602/63; 602/65
[58] Field of Search .............................. 602/5, 23, 27, 602/61–63, 65; 607/108, 111; 2/239; 36/136, 88

[56] References Cited

U.S. PATENT DOCUMENTS

| | | | |
|---|---|---|---|
| 991,831 | 5/1911 | Collis | 602/65 |
| 3,189,919 | 6/1965 | Chase | 602/63 X |
| 4,495,942 | 1/1985 | Palumbo | 602/27 |
| 4,832,010 | 5/1989 | Lerman | 602/65 X |
| 4,869,267 | 9/1989 | Grim et al. | 602/27 |
| 4,938,222 | 7/1990 | Bier, Jr. | 607/111 |
| 5,185,000 | 2/1993 | Brandt et al. | 602/65 X |

*Primary Examiner*—Linda C. M. Dvorak

[57] ABSTRACT

The Achilles Tendon Support Brace is an improved ankle support and protector of the achilles tendon; wherein two tendon supports are the key in assisting, rehabilitating and relieving pain within the achilles tendon by relieving pressure along the right and left sides of the achilles tendon.

7 Claims, 6 Drawing Sheets

ACHILLES TENDON SUPPORT BRACE

SUMMARY OF THE INVENTION

The Achilles Tendon Support Brace is used to relieve pain and or assist injured Achilles tendons in possible recovery. The brace consist of three major sections. The Exterior Ankle Support (FIG. 1, sec. 2), the Tendon Support Pouch (FIG. 2, sec. 3), and the Tendon Support (FIG. 4, sec. 4). The brace is used for individuals with one or both injured Achilles. Individuals who participate in sports can use the brace to prevent further injury or as a means of rehabilitation. The brace is also used for individuals who have problems sleeping at night due to severe pain, caused by injured Achilles tendons. In cases where pain still persist at the base of the Achilles tendon, the heel area should be wrapped with an elastic bandage.

Figure 1:
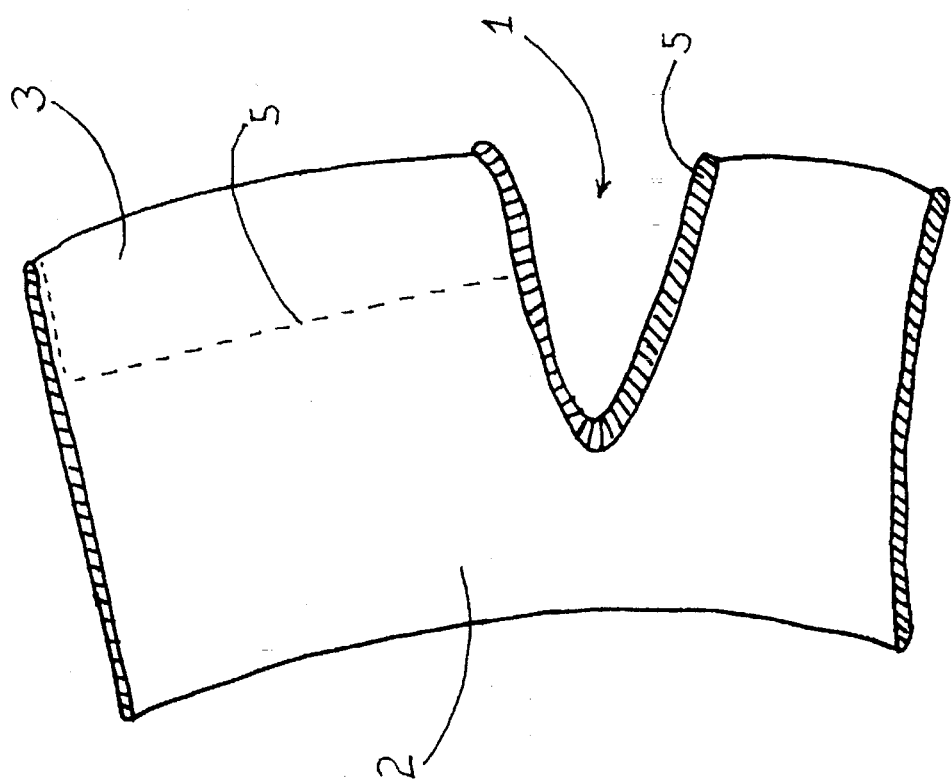
FIG. 1 shows the outside view of the Achilles Tendon Support Brace with sections labeled.
Figure 2:
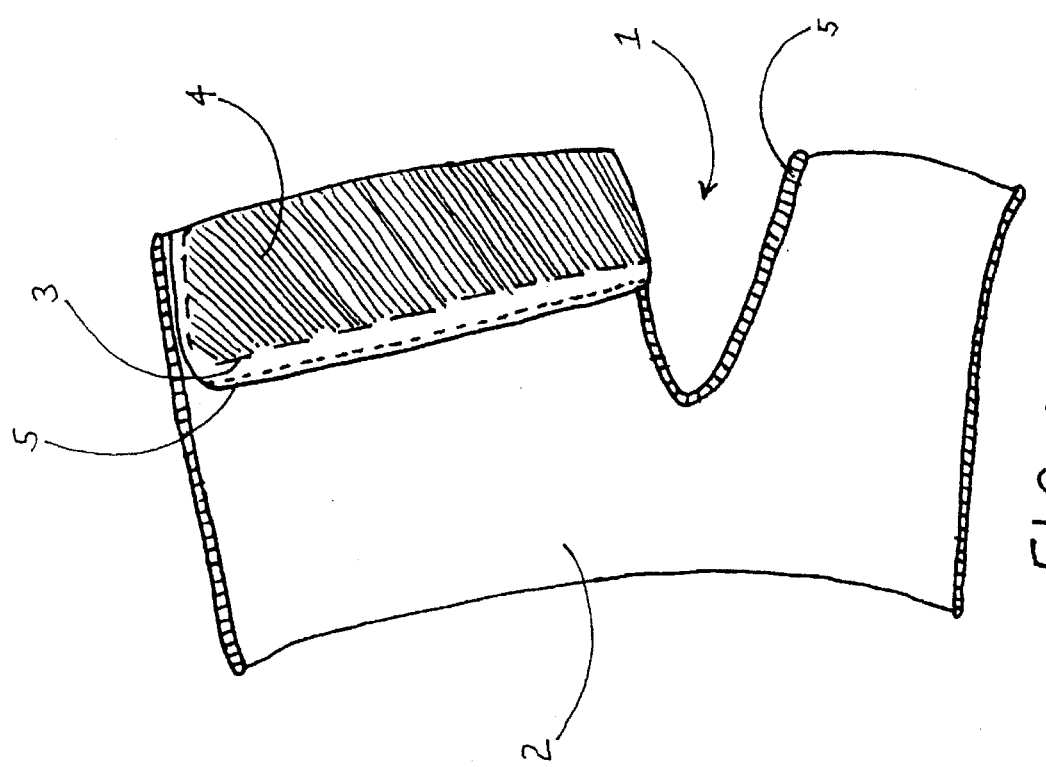
FIG. 2 shows the inside view of the Achilles Tendon Support Brace with sections labeled.

Heel Outlet (FIGS. 1 and 2, sec. 1) is provided for mobility and relief from undue pressure.

Figure 3:
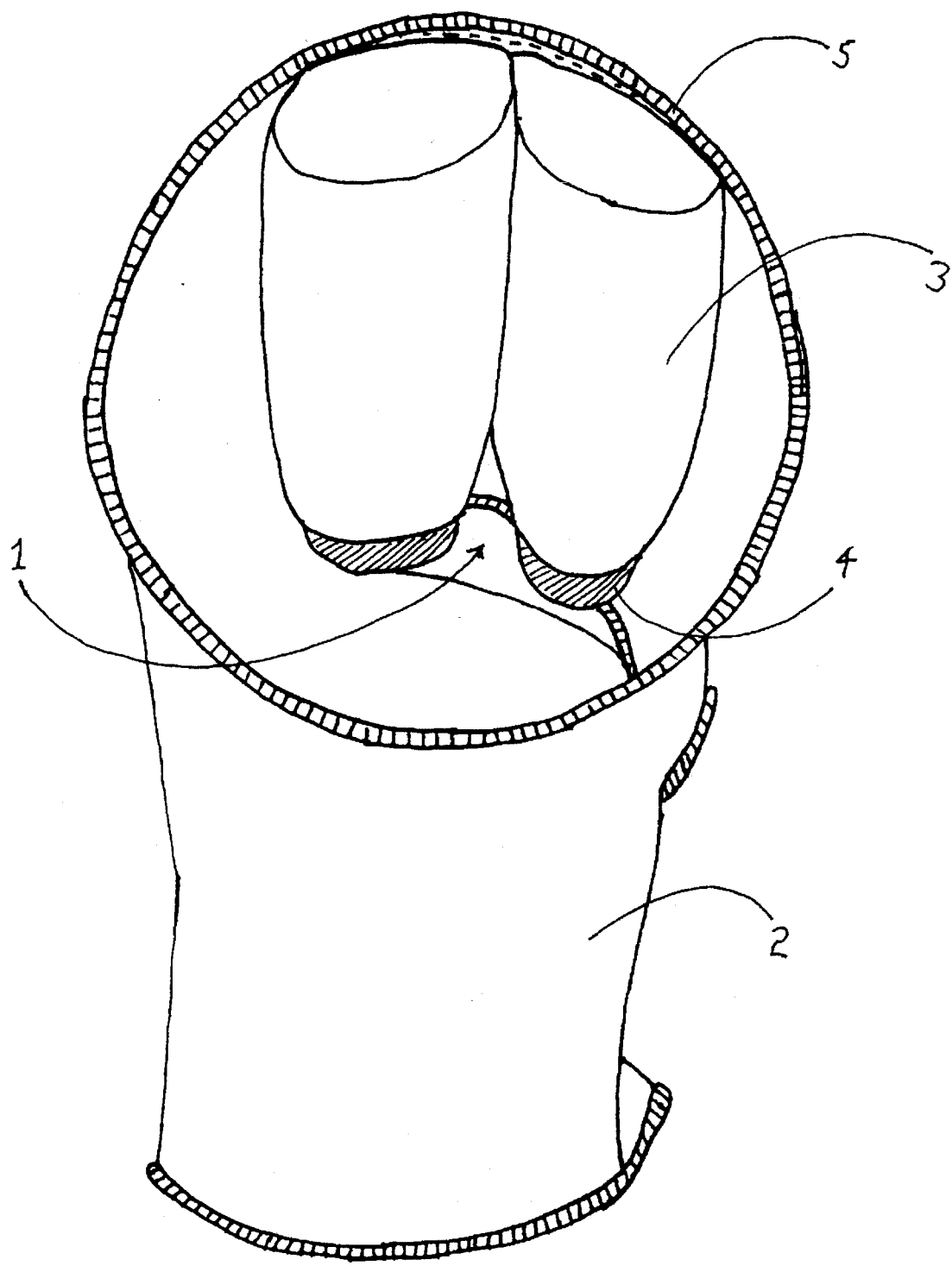
FIG. 3 shows the top view of the Achilles Tendon Support Brace with sections labeled.

Exterior Ankle Support (FIGS. 1 and 3, sec. 2) is designed to support the ankle, as well as, hold the Tendon Support Pouch (FIGS. 2 and 3, sec. 3) into place.

Tendon Support Pouch (FIGS. 2 and 3, sec. 3) is designed to hold Tendon Support(s) (FIGS. 2 and 3, sec. 4) in their proper place against the Achilles tendon(s).

Tendon Support (FIGS. 2 and 3, sec. 4) is designed to relieve pain associated with Achilles tendon injuries, and support Achilles tendon(s) during rehabilitation or during sporting activities to prevent further injury.

Seam (FIGS. 1 and 3, sec. 5) is a heavy or double stitch to prevent unraveling.

DETAILED DESCRIPTION OF THE PREFERRED EMBODIMENT

Figure 4:
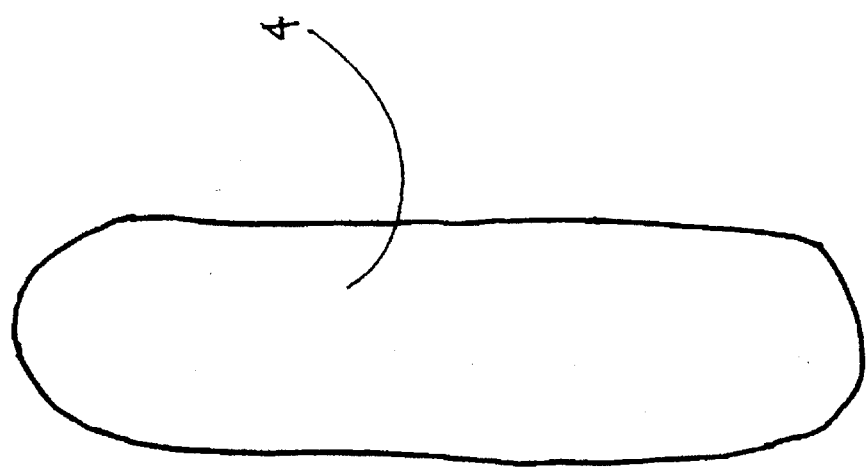
FIG. 4 shows the side view of the tendon support and its measurements.
Figure 6:
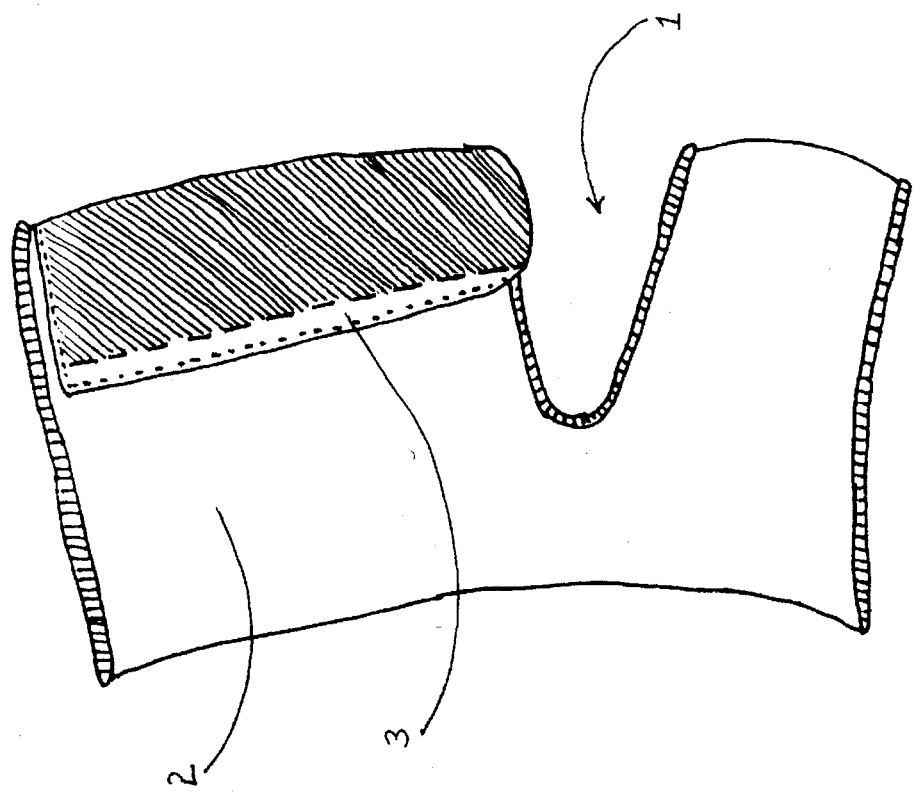
FIG. 6 shows the side view of the Achilles Tendon Support Brace and its measurements.
Figure 5:
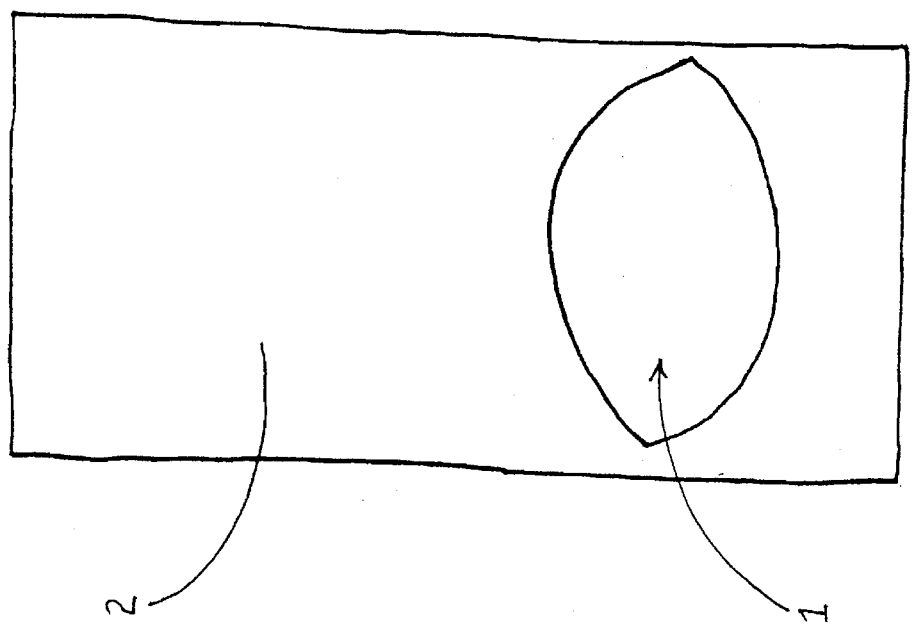
FIG. 5 shows the rear view of the Achilles Tendon Support Brace with the heel outlet.
Figure 7:
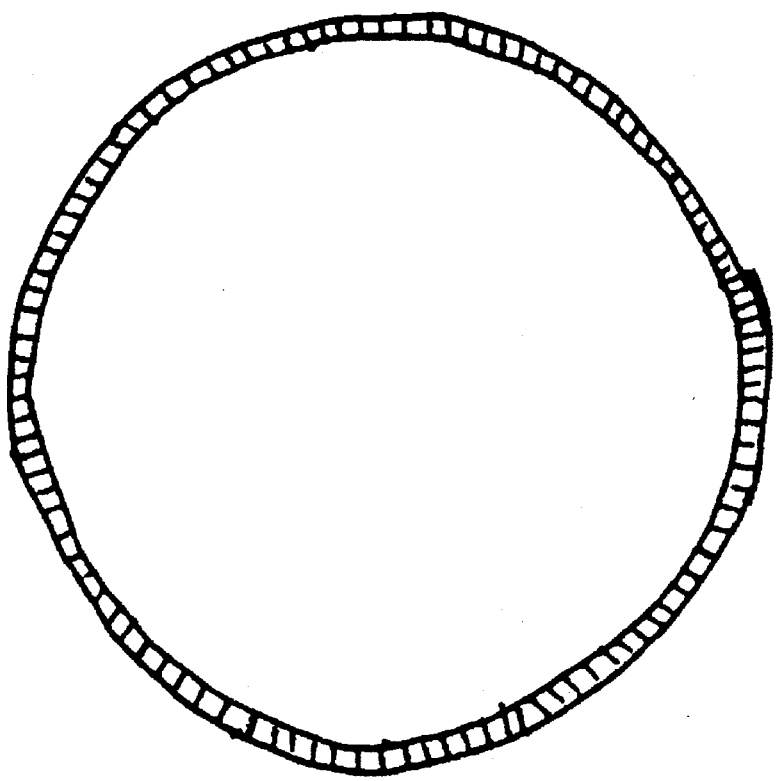
FIG. 7 shows the top view of the Achilles Tendon Support Brace and its measurement.

The Exterior Ankle Support (FIG. 1, sec. 2) is made of a strong durable elastic material to give flexibility and ensure movement. The seams (FIGS. 1 and 3, sec. 5) are heavy or double stitched thread to prevent unraveling. Approximately two thirds away from the top of the Exterior Ankle Support is a circular relief cut two to three inches in diameter, the heel outlet (FIG. 5, sec. 1). Just above the Heel Outlet (FIG. 6, sec. 1) and below the top of the Exterior Ankle Support (FIG. 6, sec. 2) and on the inside of the Exterior Ankle Support is the Tendon Support Pouch (FIG. 6, sec 3), made of a strong durable elastic material for flexibility. The Tendon Support Pouch (FIG. 6, sec 3) is stiched in the center of the Exterior Ankle Support (FIG. 6, sec 2), between the middle of the Heel Outlet (FIG. 6, sec 1) and the top of the Exterior Ankle Support (FIG. 6, sec 2). Another stitch is located just opposite the previous stitch forming a pouch or pocket with the lower or bottom portion open. Tendon Supports (FIG. 4, sec. 4) are tubular cylinders one inch in diameter and three to four inches in length. They are made of a flexible substance (¾ inch tubular guaze covered with plastic or rubber, cylinders made of rubber, air filled cylinders or gelatin filled cylinders), anything capable of forming or molding to each individual ankle. Tendon Support (FIG. 4, sec 4) are placed inside the Tendon Support Pouch (FIGS. 2 and 3, sec 3) along the side of the Achilles tendon(s), on the right and left side of the injured Achilles tendon(s). Tendon Supports (FIG. 4, sec. 4) should not rest on bones or heel to prevent irritation.

I claim:

1. A dynamic sleeve-shaped ankle brace for supporting an ankle of lower extremity comprising:

a sleeve having an upper end, a lower end, an anterior portion, and a posterior portion; said sleeve having an ankle receiving opening at its upper end, a toe receiving opening at its lower end, and a heel outlet in the posterior portion; said sleeve additionally comprising at least one tendon support pouch in said posterior portion above said heel outlet; and a tendon support comprising two flexible cylinders positionable in said at least one tendon support pouch; one each of said two flexible cylinders adapted to be positioned along side the right and left sides, respectively, of the Achilles tendon;

wherein when said brace is in use, pressure is relieved from along the right and left sides of the Achilles tendon by diverting pressure to surrounding areas.

2. A dynamic sleeve-shaped ankle brace according to claim 1 wherein the top portion of said at least one tendon support pouch is connected to the upper interior of said sleeve, and the sides of said at least one tendon support pouch are connected to the interior of said sleeve thereby forming said at least one tendon support pouch with an opening located at the bottom of said pouch.

3. A dynamic sleeve-shaped ankle brace according to claim 1 wherein said sleeve and said at least one tendon support pouch are made of flexible material to ensure movement when the foot is in motion.

4. A dynamic ankle brace according to claim 1 wherein the flexible cylinders are made of flexible rubber.

5. A dynamic ankle brace according to claim 1 wherein the flexible cylinders are made of gauze covered with a flexible plastic or rubber.

6. A dynamic ankle brace according to claim 1 wherein the flexible cylinders are made of a hollow flexible plastic or rubber filled with air.

7. A dynamic ankle brace according to claim 1 wherein the flexible cylinders are made of a flexible plastic or rubber filled with gelatin.

* * * * *